United States Patent [19]

Ghodsian

[11] Patent Number: 5,256,139
[45] Date of Patent: Oct. 26, 1993

[54] INTRA-ABDOMINAL ORGAN MANIPULATOR, IRRIGATOR, ASPIRATOR AND METHOD

[76] Inventor: Kamran Ghodsian, 1522 Valencia, Newport Beach, Calif. 92660

[21] Appl. No.: 836,413

[22] Filed: Feb. 18, 1992

Related U.S. Application Data

[62] Division of Ser. No. 637,592, Jan. 3, 1991, Pat. No. 5,197,948.

[51] Int. Cl.$^5$ ............................................. A61M 31/00
[52] U.S. Cl. ........................................ 604/49; 604/28
[58] Field of Search ............... 604/27, 28, 35, 39, 604/49, 54, 96, 101, 102; 606/192–196

[56] References Cited

U.S. PATENT DOCUMENTS

| | | | |
|---|---|---|---|
| 2,849,002 | 8/1958 | Oddo | 606/192 |
| 4,089,337 | 5/1978 | Kronner | 604/96 |
| 4,356,824 | 11/1982 | Vazquez | 604/35 |
| 4,430,076 | 2/1984 | Harris | 604/96 |
| 5,078,725 | 1/1992 | Enderle et al. | 606/193 |
| 5,104,377 | 4/1992 | Levine | 606/193 |

*Primary Examiner*—John D. Yasko
*Assistant Examiner*—Anthony Gutowski
*Attorney, Agent, or Firm*—Harold L. Jackson

[57] ABSTRACT

A method of using an intra-abdominal organ manipulator, irrigator and/or aspirator, which includes a tubular probe member with distal and proximal ends and a through lumen extending the length thereof, is described. A balloon is affixed to the distal end to aid in manipulating organs or parts thereof within the abdominal cavity when inflated through an auxiliary lumen in the probe. A handle attached to the proximal end of the probe has a pair of trumpet valves which allow the user to connect a vacuum source or irrigation fluid source to the through lumen.

2 Claims, 2 Drawing Sheets

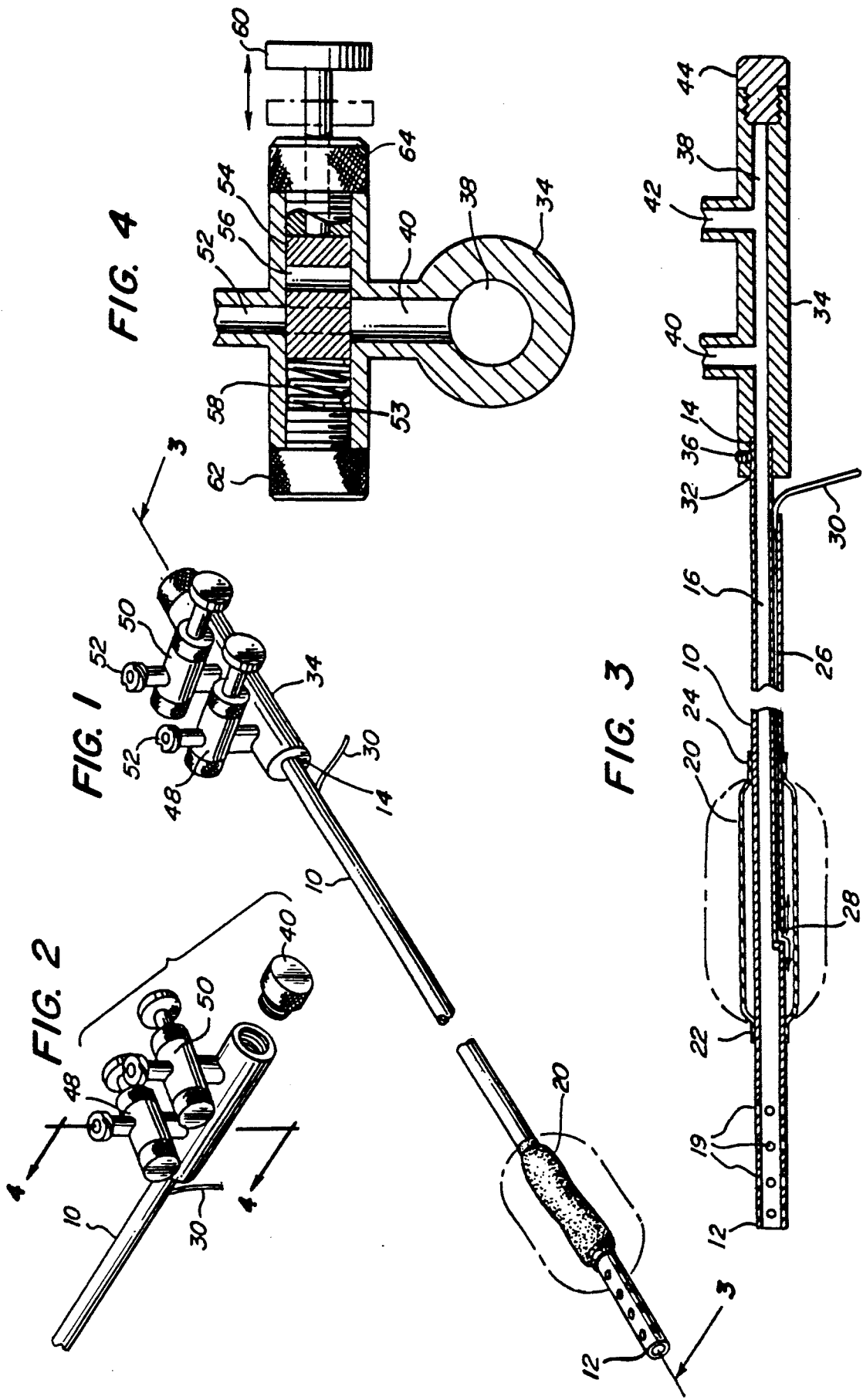

INTRA-ABDOMINAL ORGAN MANIPULATOR, IRRIGATOR, ASPIRATOR AND METHOD

RELATED APPLICATION

This application is a division of application serial no. 07/637,592, filed Jan. 3, 1991 for and INTRA-ABDOMINAL ORGAN MANIPULATOR, IRRIGATOR ASPIRATOR AND METHOD (now U.S. Pat. No. 5,197,948).

BACKGROUND OF THE INVENTION

1. Field of the Invention

The present invention relates to the surgical instrument art and more particularly to a surgical instrument and method for manipulating, irrigating and aspirating organs and tissue within a surgical area in the abdominal cavity.

2. Description of the Prior Art

In many surgical procedures within the abdominal cavity it is important and difficult to move or manipulate organs or parts thereof (such as sections of the bowel) in order to observe and operate on a particular organ or tissue section within that cavity. It is also often necessary to flush (irrigate) the surgical area with an appropriate fluid (e.g., antiseptic) and/or remove (aspirate) fluid from the area during the operation. Prior art instruments for irrigation and aspiration purposes are available in the form of elongated tubes open at the distal end and equipped with finger operated valves for connecting a source of fluid or vacuum source to the tube. However, such prior art irrigation and aspiration devices which provide only a small tubular tip within the abdominal cavity are ill equipped to manipulate organs or parts thereof so that the surgeon (user) can readily locate the area or organ of interest.

Other prior art devices such as the one described in U.S. Pat. No. 4,744,363 ("'363 patent") are designed so that the tip of the instrument is in the form of a relatively stiff split sleeve which may be expanded to provide a greater surface area with which to move an organ out of the way. The split sleeve would not provide a smooth continuous surface with which to manipulate organs or tissue. Also the '363 device would not readily accommodate structure for irrigating and/or aspirating the surgical area. U.S. Pat. Nos. 4,617,013 and 4,759,349 disclose instruments for irrigating, aspirating and illuminating surgical areas. However, these instruments are designed for use in an open abdomen instead of in a closed abdomen (laparoscopy). Furthermore, such prior art instruments are complicated and do not provide any convenient means for moving organs or tissue out of the way to facilitate surgery or other treatment on the desired organ or tissue.

The above disadvantages as well as others inherent in the prior art devices are overcome by the present invention.

SUMMARY OF THE INVENTION

In accordance with the present apparatus a surgical instrument for enabling a surgeon to manipulate, irrigate and aspirate organs within a surgical area includes a tubular probe with distal and proximal ends and a through lumen. The instrument of this invention may be used in an open or closed abdominal surgery (e.g., laparotomy, laparoscopy respectively). The distal end of the probe is open and preferably that end defines a plurality of holes so that fluid may pass from the through lumen to the surgical area surrounding the distal end of the probe via the holes and open distal end and visa versa. A handle member is attached to the proximal end of the probe and includes a central passageway therein connected to the through lumen so that fluid can be supplied to or removed from the body cavity or organ in which the distal end of the probe is inserted.

An inflatable balloon is secured to the exterior of the probe adjacent the distal end so that the interior of the balloon is isolated from the through lumen. An auxiliary lumen extends along the length of the probe and is in fluid communication with the interior of the balloon so that fluid may be supplied to or removed from the interior of the balloon to inflate and deflate the same.

In accordance with the present method the distal end of the probe described above is inserted into the surgical area. The balloon is then inflated and the distal end of the probe and the inflated balloon are positioned against the organ or part thereof to be moved. The distal end of the probe is then moved until the organ or part thereof is repositioned as desired and the surgical procedure completed. The balloon is then deflated and the probe withdrawn.

The features of the present invention can best be understood by reference to the following description, taken in conjunction with the accompanying drawings wherein like numerals indicate like parts.

BRIEF DESCRIPTION OF THE DRAWINGS

FIG. 1 is a perspective view of a medical probe and handle in accordance with the present invention;

FIG. 2 is a enlarged perspective view of a portion of the probe and handle of the instrument of FIG. 1;

FIG. 3 is a cross-sectional view of the instrument taken along lines 3—3 in FIG. 1; and FIG. 4 is a cross-sectional view of one of the finger operated trumpet valves for controlling the flow of fluid to or from the handle of the instrument taken along lines 4—4 in FIG. 2.

DESCRIPTION OF THE PREFERRED EMBODIMENT

Figure 5:
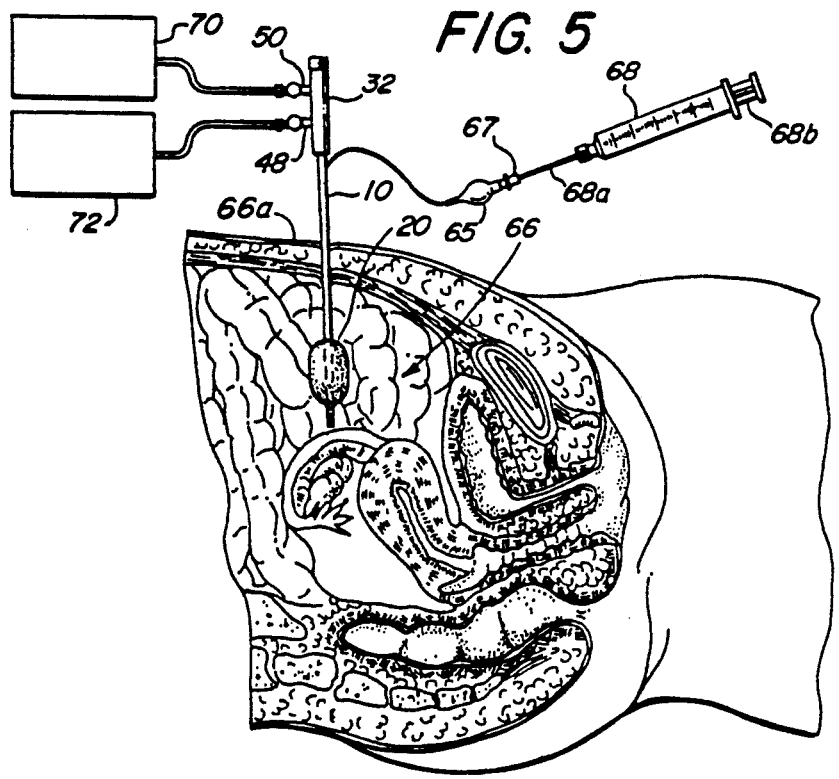
FIG. 5 is a schematic diagram showing the instrument of FIG. 1 in use.

Referring now to the drawings and more particularly to FIGS. 1-3, the medical instrument includes an elongated tubular probe member 10. The probe 10 has a distal end 12 and a proximal end 14. A passageway or through lumen 16 extends the length of the probe 10 from its open distal end to its proximal end 14. A plurality of holes 19 are arranged in the wall of the probe adjacent its distal end 12 as illustrated. An inflatable flexible membrane in the form of a balloon 20 has its outer ends 22 and 24 secured in an airtight manner to the outer periphery of the tubular probe 10 adjacent the holes 19. The probe includes an additional passageway or auxiliary lumen 26 extending along its length in fluid communication with the interior of the balloon 20 via opening 28 in the probe wall. The auxiliary lumen terminates in a flexible tube 30 adjacent the proximal end 14 of the probe 10. Fluid may be injected into or withdrawn from the tube 30 to inflate or deflate the balloon 20 as will be explained more fully in conjunction with FIG. 5.

The proximal end of the probe 10 is slidably received in a bore 32 of a handle member 34. A set screw 36 secures the handle and probe together. The handle defines a central passageway 38, an aspiration port 40 and an irrigation port 42 in fluid communication with the through lumen 16 as shown in FIG. 3. A threaded plug 44 closes the end of the central passageway 38 in the handle 34.

Finger actuated trumpet valves 48 and 50 are connected in the aspiration and irrigation ports 40 and 42, respectively. The valve bodies may be formed integrally with the handle 34 as is illustrated in FIG. 4. Each valve includes an inlet port 52, a lateral passageway 53 which accommodates a sliding valve member 54 with a passageway 56, a compression spring 58 which biases the valve member 54 in the closed position (shown in FIG. 4), and a finger operated plunger 60 connected to the valve member 54 for opening the valve in response to a user's finger pressure. Threaded plugs 62 and 64 close the passageway 53.

The tubular probe 10 and the handle 32 may be manufactured of metal such as stainless steel. Preferably the probe 10 is made of a carbon impregnated plastic such as PVC, vinyl or epoxy so that when exposed to laser radiation it will not inflame and burn the surrounding tissue. The probe 10 may be disposable to eliminate the need for sterilization after use. The outer diameter of the probe 10 is preferably within the range of about 3-6 mm and most preferably about 4 mm. The diameter of the through lumen 16 is preferably within the range of 1-5 mm and most preferably about 3 mm. The length of the probe 10 is preferably about 25 cm.

Figure 6:
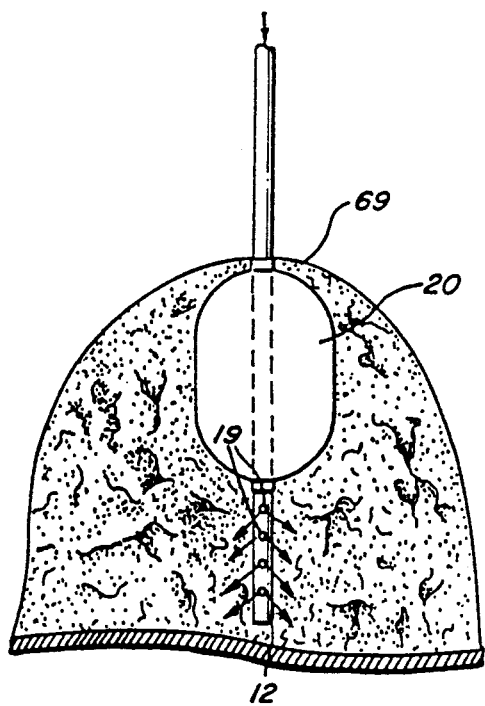
FIG. 6 is a cross-sectional view of the distal end of the probe inserted into a cyst, organ or surgical area illustrating the method of irrigating such area.
Figure 7:
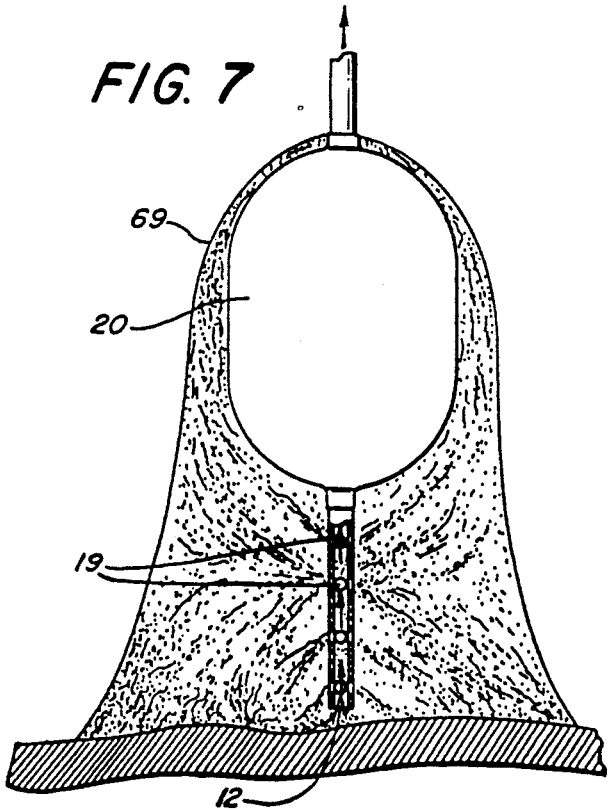
FIG. 7 is a cross-sectional view of the distal end of the probe inserted into a cyst, organ or surgical area illustrating the method of aspirating or removing fluid from such area.

Referring now to FIGS. 5-7, the distal end of the probe member 10 with the balloon 20 deflated is inserted through an incision in the abdominal cavity via a conventional trocar sleeve (not shown). The balloon is then inflated with a fluid such as a gas (i.e., air) or a liquid (e.g., water) to an appropriate diameter e.g., 20-30 mm via a valved flexible receptacle 65 and a syringe or other source of pressurized fluid 68. The valved receptacle is connected to the flexible tube 30 and includes a spring loaded normally closed valve (not shown) in the end 67 thereof. The needle 68a at the end of the syringe opens the valve to allow fluid to enter the tube 30. Once the balloon is inflated the syringe may be removed from the valved receptacle. The appearance of the receptacle 65, i.e., whether extended or collapsed, informs the user or surgeon of the condition of the balloon 20, i.e., whether inflated or deflated.

Once the balloon 20 is inflated, the probe's distal end with the inflated balloon is positioned against an organ or part thereof (e.g., the bowel) to be moved. The distal end is then moved until the organ or part thereof is repositioned as desired. To aid in manipulating the organ, the balloon may be provided with a roughened surface as is illustrated, for example, in FIG. 5, to increase its surface friction. The surgical area into which the distal end has been inserted may then be irrigated to flush the area or aspirated to remove fluid or solid material from the area or organ. The irrigating liquid may be supplied from a suitable source 70 of such liquid under pressure via the finger operated valve 50. Liquid and/or solids may be removed for the surgical area or organ by connecting the through lumen 10 of the probe to a suitable vacuum source 72 via valve 48. The balloon may be deflated for removal from the abdominal cavity by withdrawing fluid through the auxiliary lumen via the receptacle 65 and syringe 68.

The distal end of the probe may also be inserted into an organ (e.g., gall bladder) or growth such as a cyst 69 while the balloon is deflated. Once the distal end and balloon is within the cyst 69 the balloon may be inflated and positioned against the point of entry to provide a sealing action against the cyst wall to minimize the leakage of fluid from the cyst (or organ) into the abdominal cavity as is shown in FIGS. 6 and 7. The interior of the cyst may be irrigated as is illustrated in FIG. 6 or aspirated as is illustrated in FIG. 7.

There has thus been described a intra-abdominal organ manipulator, irrigator and/or aspirator and method of using the same. Various modifications will be apparent to those skilled in the art without involving any departure from the spirit and scope of my invention as defined in the appended claims.

What is claimed is:

1. A method of manipulating organs or parts thereof within a patient's abdominal cavity and aspirating the interior of an organ, growth or cyst located within said cavity with a surgical probe having distal and proximal ends, a through lumen open at the distal end, an inflatable balloon affixed to the exterior of the probe adjacent the distal end thereof and means for inflating/deflating the balloon and for selectively connecting the through lumen to a low pressure source comprising the steps of:
   a) manually inserting the distal end of the probe into the abdominal cavity so that the probe end is positioned outside of the organ to be manipulated;
   b) inflating the balloon;
   c) positioning the balloon and distal end of the probe against the organ or part thereof to be moved;
   d) moving the distal end of the probe until the organ or part thereof is repositioned as desired;
   e) deflating the balloon;
   f) manually inserting the distal end of the probe into the organ, growth or cyst to be aspirated;
   g) inflating the balloon;
   h) positioning the balloon against the interior wall of the organ, growth or cyst adjacent the point of entry to minimize the leakage of fluid from the organ growth or cyst into the abdominal cavity;
   i) connecting the through lumen to the low pressure source to aspirate fluid from the organ growth or cyst;
   j) deflating the balloon; and
   k) withdrawing the probe.

2. The method of claim 1 wherein the probe further includes means for selectively connecting the through lumen to a source of irrigation fluid and further including the step of connecting the through lumen to the source of irrigation fluid while the distal end of the probe is inserted into the organ, growth or cyst to irrigate the organ, growth or cyst.

* * * * *